United States Patent [19]

Nonaka et al.

[11] Patent Number: 5,929,280
[45] Date of Patent: Jul. 27, 1999

[54] PROCESS FOR THE PREPARATION OF AQUEOUS SOLUTIONS OF TETRAALKYLAMMONIUM HYDROXIDES

[75] Inventors: Tooru Nonaka; Yasunori Hirata; Masafumi Shibuya, all of Tokuyama, Japan

[73] Assignee: Tokuyama Corporation, Yamaguchi-ken, Japan

[21] Appl. No.: 09/043,564

[22] PCT Filed: Jul. 18, 1997

[86] PCT No.: PCT/JP97/02505

§ 371 Date: Mar. 23, 1998

§ 102(e) Date: Mar. 23, 1998

[87] PCT Pub. No.: WO98/03466

PCT Pub. Date: Jan. 29, 1998

[30] Foreign Application Priority Data

| Jul. 23, 1996 | [JP] | Japan | 8-193601 |
| Jul. 31, 1996 | [JP] | Japan | 8-202052 |
| Jul. 23, 1997 | [JP] | Japan | 86110474 |

[51] Int. Cl.⁶ ............... C07C 209/00; C07C 209/12; C07C 209/84
[52] U.S. Cl. .................................................. 564/296
[58] Field of Search ................................... 564/296

[56] References Cited

FOREIGN PATENT DOCUMENTS

| 127201 | 12/1984 | European Pat. Off. . |
| 56-156239 | 12/1981 | Japan . |
| 57-099559 | 6/1982 | Japan . |
| 57-139042 | 8/1982 | Japan . |
| 59-193289 | 11/1984 | Japan . |
| 60-131985 | 7/1985 | Japan . |
| 63-233956 | 9/1988 | Japan . |
| 2-073024 | 3/1990 | Japan . |
| 3-167160 | 7/1991 | Japan . |
| 4-228587 | 8/1992 | Japan . |
| 6-056712 | 3/1994 | Japan . |
| 6-173054 | 6/1994 | Japan . |
| 6-329602 | 11/1994 | Japan . |

*Primary Examiner*—Peter O'Sullivan
*Attorney, Agent, or Firm*—Birch, Stewart, Kolasch & Birch, LLP

[57] ABSTRACT

There is provided a simple method of producing in a good yield a tetraalkylammonium hydroxide aqueous solution in which the content of metal ions such as alkali metal ions is reduced to an extremely low level.

High-purity trialkylamine and high-purity alkyl chloride are reacted with each other in ultrapure water to obtain an extremely high-purity tetraalkylammonium chloride aqueous solution substantially free from metal ions such as alkali metal ions, and then, the tetraalkylammonium chloride aqueous solution is subjected to electrolysis-dialysis in a solution state without drying it into a solid to produce a tetraalkylammonium hydroxide aqueous solution. Thereby, an extremely high-purity tetraalkylammonium hydroxide aqueous solution with little reduction in purity is obtained in a high yield.

9 Claims, 1 Drawing Sheet

PROCESS FOR THE PREPARATION OF AQUEOUS SOLUTIONS OF TETRAALKYLAMMONIUM HYDROXIDES

This application is the national phase under 35 U.S.C. §371 of prior PCT International Application No., PCT/JP97/02505, which has an International filing date of Jul. 18, 1997, which designated the United States of America, the entire contents of which are hereby incorporated by reference.

FIELD OF TECHNOLOGY

This invention relates to a novel method of producing efficiently tetraalkylammonium hydroxide (may be abbreviated as TAAH hereinafter) aqueous solution having extremely high-purity.

BACKGROUND OF THE INVENTION

A TAAH aqueous solution is a useful chemical as a strong base in a chemical reaction and has been recently used also as a processing chemical in a semiconductor-related field, such as the cleaning and etching of a semiconductor substrate and the development of a resist in the production of ICs and LSIs.

For use as a processing chemical in the semiconductor-related field, a high-purity tetraalkylammonium hydroxide aqueous solution containing no impurities such as metal ions and organic substances has been desired, along with progress made in the integration of semiconductor devices.

Heretofore, the above TAAH aqueous solution has been produced by dissolving solid tetraalkylammonium chloride (may be abbreviated as TAAC hereinafter) in water to prepare a TAAC aqueous solution and electrolyzing and electrodialyzing the TAAC aqueous solution to effect ion-exchange between chlorine ions and hydroxyl ions.

In the above production method of the TAAH aqueous solution, reasons why TAAC is used in a solid state are as follows. That is, TAAC has been heretofore produced by reacting a trialkylamine with an alkyl chloride in a polar solvent such as water, isopropanol or the like. However, in the industrial production, water as a solvent has been rarely used actually and an organic solvent such as isopropyl alcohol has been generally used.

Therefore, to prepare a TAAC aqueous solution, there is employed a method in which solid TAAC obtained by drying a TAAC aqueous solution to remove the solvent is dissolved in water. This is one of the reasons for handling TAAC in a solid state.

Another reason is that TAAC is generally used as an additive such as a phase-transfer catalyst or reagent and it must be solid when it is directly added to a reaction system.

Still another reason is that solid TAAC is advantageous in transportation between factories, handling and the like.

However, the above-mentioned application involves problems. That is, the method of producing a TAAH aqueous solution from the above solid TAAC requires a process of drying TAAC into a solid. Therefore, concentrated metal impurities such as metal ions derived from a solvent and raw materials are contained in TAAC, and further, when TAAC is dissolved in water, impurities contained in water are added thereto. Consequently, the purity of the obtained TAAH aqueous solution is greatly lowered.

Further, at the time of drying, TAAC is partially decomposed, whereby the yield thereof is lowered and at the same time, the purity of the obtained TAAH aqueous solution is lowered by the decomposition product, like in the above case.

Meanwhile, use of purified TAAC as a raw material of the TAAH aqueous solution to improve the purity of the TAAH aqueous solution is known as disclosed in Japanese Laid-open Patent Application 60-131985 (131985/1985), for example. The above publication teaches that the impurities of alkali metals and alkaline earth metals out of impurities derived from raw materials can be reduced to such an extent that a required purity of a quaternary hydroxide can be obtained by selecting a quaternary ammonium salt as a raw material with care and purifying it.

However, TAAC cannot be purified by distillation due to its properties, and the industrial-scale purification thereof is limited to a separation method in an ion state such as electrodialysis. For example, when are purification is conducted by letting quaternary ammonium ions passing through a cation exchange membrane, most of alkali metal ions pass through a separating membrane together with tetraalkylammonium ions in the purification because alkali metal ions have a smaller ion diameter than tetraalkylammonium ions. Meanwhile, for removing alkali metal ions by a univalent perm-selective membrane completely, it takes extremely long time and hence, this is not practical.

Therefore, it has been difficult to purify TAAC to such an extent that the concentration of alkali metal ions is several ppb, which is the target of the present invention, with the conventional method.

The purification by electrodialysis of the obtained TAAH aqueous solution is disclosed also in Japanese Laid-open Patent Application 60-131985. According to this publication, a means to purify the TAAH aqueous solution containing the above impurities comprises supplying the TAAH aqueous solution to be purified to an anode chamber formed by installing a cation exchange membrane between an anode and a cathode, supplying water to a cathode chamber and applying electricity between the both electrodes to obtain purified TAAH from the cathode chamber.

However, in this case, too, the removal of univalent ions such as sodium and potassium is not sufficient like the purification of the aforesaid TAAC aqueous solution and hence, an extremely high-purity TAAH aqueous solution does not yet come to be obtained.

As described above, in any of the above conventional methods for obtaining a high-purity TAAH aqueous solution, purification is carried out in a condition that separation of metal ions such as sodium and potassium is difficult to conduct, and the level of high purity thereof is required to be further improved.

DISCLOSURE OF THE INVENTION

It is therefore an object of the present invention to provide a simple method of producing in a high yield a TAAH aqueous solution in which the content of metal ions such as alkali metal ions is reduced to an extremely low level.

The inventors of the present invention have conducted diligent studies to attain the above object, and found that it is possible to remove metal ions on a high level from an trialkylamine and alkyl chloride, which are raw materials of TAAC, by distillation, and an extremely high-purity TAAC aqueous solution substantially free from metal ions such as alkali metal ions can be obtained by causing them to react with each other in ultrapure water, and that an extremely high-purity TAAH aqueous solution with little reduction in purity can be obtained in a high yield by producing a TAAH aqueous solution by electrodialysis in an aqueous solution state without drying it into a solid. The present invention has been accomplished based on these findings.

That is, the present invention is a method of producing a high-purity tetraalkylammonium hydroxide aqueous solution comprising the steps of:

reacting trialkylamine and alkyl chloride, both having a metal ion impurity content of 500 ppb or less, in ultrapure water to form an aqueous solution of tetraalkylammonium chloride, and subjecting the resulting aqueous solution of tetraalkylammonium chloride to electrolysis and electrodialysis to produce a high-purity tetraalkylammonium hydroxide aqueous solution.

Figure 1:
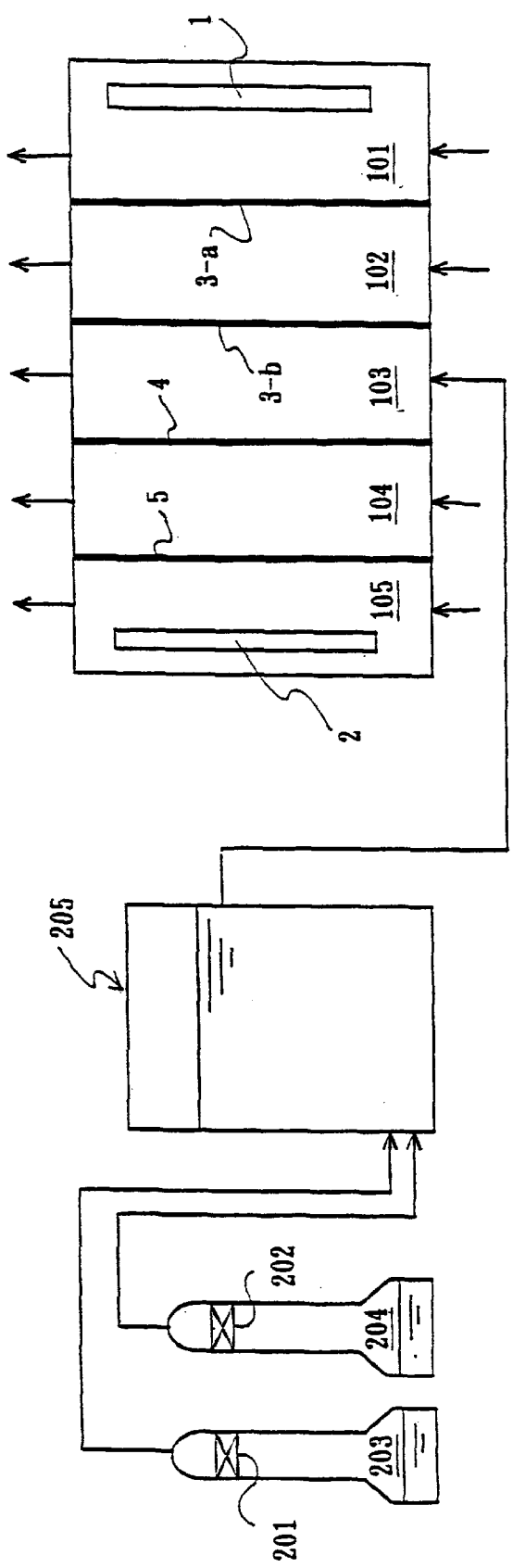
FIG. 1 is a schematic diagram of preferred examples of a reactor and an electrolysis and electrodialysis cell used for carrying out the method of the present invention.

In the drawing, reference numeral 1 denotes a cathode, 2 anode, 3-a and 3-b cation exchange membranes, 4 anion exchange membrane, 5 cation exchange membrane, 101 a cathode chamber, 102 to 104 intermediate chambers, 105 an anode chamber, 201 and 202 demisters, 203 and 204 distillation columns and 205 a reactor.

DETAILED DESCRIPTION

In the present invention, any trialkylamine that is soluble in water at a reaction temperature can be used without particular restriction. The method of the present invention is suitable for trialkylamines having an alkyl group with 1 to 4 carbon atoms, particularly suitable for trimethylamine.

Any alkyl chloride that is soluble in water at a reaction temperature can be used also without particular restriction. The method of the present invention is suitable for alkyl chlorides having an alkyl group with 1 to 4 carbon atoms, particularly suitable for methyl chloride.

To obtain a TAAC aqueous solution at a high-purity, it is important to remove metal impurities such as metal ions contained in the trialkylamine and alkyl chloride, which are the raw materials of the above reaction, before subjecting them to the reaction. That is, a process for removing impurities from the TAAC aqueous solution containing impurities such as metal ions is extremely complicated, and invites an inclusion of impurities produced by the decomposition of TAAC in the removing process step and as a result, a reduction in the yield of TAAC even if the impurities can be removed.

Therefore, it is preferred that the above removal operation for purification is carried out to such an extent that the concentration of metal ion impurities contained in the raw materials is preferably 500 ppb or less, more preferably 100 ppb or less.

As the method of removing the above metal impurities for purification, a method by distillation is suitable. In the case where the trialkylamine and alkyl chloride are gaseous at normal temperature, that is, in the case of trimethylamine and methyl chloride, liquefied products thereof are subjected to distillation. In this case, to prevent a purified material from being mixed with metal impurities by entrainment, demisters 201 and 202 are desirably installed in top portions of distillation columns 203 and 204, respectively, as shown in FIG. 1.

In the present invention, a reaction between trialkylamine and alkyl chloride is carried out using ultra-pure water as a solvent. As far as the reaction is carried out in ultrapure water, other conditions are not particularly limited. In this specification, there is preferably used ultrapure water having a resistivity of 18.0 MΩ·cm or more and containing particles having a particle diameter of 0.2 μm or more at a density of one particle per 10 cc or less.

The reaction is carried out in a reactor filled with ultrapure water. The trialkylamine and alkyl chloride, which are raw materials, may be supplied in a liquid or gaseous state. For example, when the above trimethylamine and methyl chloride are used, they are supplied preferably in a gaseous state. In this case, part of the gases is dissolved in ultrapure water and the reaction proceeds in the ultrapure water. As a matter of course, it is possible to supply these raw materials in a liquid state above atmospheric pressure and partially dissolve them in the ultrapure water to carry out a reaction. As the case may be, it is also possible that one or both of the raw materials may be dissolved in the ultrapure water solvent and then supplied to a reaction system.

Any reaction conditions are acceptable without particular limitation if the raw materials can be dissolved in the ultrapure water. The reaction temperature is preferably 5 to 80° C., more preferably 20 to 60° C. The reaction pressure is preferably 0 to 9.9 kg/cm$^2$, particularly preferably 0 to 4 kg/cm$^2$. As for the amounts of trialkylamine and alkyl chloride to be supplied for the reaction, the molar ratio of trialkylamine to alkyl chloride is generally selected from the range of 1:1 to 1:1.5. Particularly, the ratio is preferred to be 1:1.2 to 1:1.5 such that the alkyl chloride which can be easily removed from the solution after the reaction by evaporation to be described later becomes excessive in quantity. Further, the reaction time which slightly differs according to the kinds of the raw materials cannot be limited definitely but is generally 1 to 24 hours, particularly suitably 1 to 5 hours.

After the reaction, operation (aging) for elevating temperature by 50 to 60° C. from the reaction temperature and maintaining that temperature for 1 to 5 hours is preferably carried out to further increase the yield of the reaction.

In order to prevent metal ions from being eluted out from the devices into a TAAC aqueous solution and a TAAH aqueous solution that is the end product, it is preferred that at least the inside surfaces of a reactor for obtaining the TAAC aqueous solution and an electrolysis and electrodialysis cell for electrolyzing and electrodialyzing the TAAC aqueous solution should be made from a material which does not elute metal ions substantially, and these devices should be connected by an airtight pipe of which at least inside surface is made from a material which does not elute metal ions substantially. The material which does not elute metal ions substantially is selected from fluororesins such as polytetrafluoroethylene (PTFE) and PFA and other resins such as polypropylene (PP), polyethylene (PE), polyvinyl chloride (PVC) or the like. Of these, the treatment by fluororesins such as PTFE and PAF is the most preferred.

Means for constituting these devices using the material that does not elute metal ions substantially is to form all the parts of the device from such material or line the surfaces of all the parts of the device with the material.

In the present invention, unreacted raw materials are removed from the TAAC aqueous solution obtained by the above reaction, and evaporation operation is carried out as required until an appropriate concentration is obtained.

When the unreacted raw materials are to be removed, the conditions of a temperature of 50 to 60° C. and a operation time of 1 to 5 hours are generally employed for evaporation operation. Topping using nitrogen or inert gas may be used as required.

To use the obtained TAAC aqueous solution as a raw material of the TAAH aqueous solution, the TAAC aqueous solution preferably has a concentration of 40 to 50 wt % and, as required, evaporation operation is carried out until such concentration is obtained.

The removal and/or concentration of the unreacted materials is preferably carried out by heating the TAAC aqueous solution at a reduced pressure of $10^5$ to 10 Pa.

The unreacted materials removed by the above operation and distilled out in a gaseous state together with part of water are preferably collected, and recycled as required. For example, when methyl chloride is a main unreacted material, it is recommended that its gaseous distillate be brought into contact with the above ultrapure water to be dissolved therein and collected, because it has a low boiling point and is difficult to be condensed. The ultrapure water which has absorbed the unreacted material may be recycled to the above reaction system.

Further, in the removal of the unreacted materials, the solution is desirably maintained at an alkaline level, for example, pH of 8 or more, preferably 8 to 12. The high-purity TAAH aqueous solution obtained by the present invention is advantageously used to adjust the pH.

Since the TAAC aqueous solution obtained by the method of the present invention does not need to be dried and re-dissolved in water unlike TAAC obtained by the prior art method, it can be used in the production of a TAAH aqueous solution while retaining high purity.

In this connection, the content of metal ion impurities in the TAAC aqueous solution is 500 ppb or less, preferably 100 ppb or less, based on TAAC. Particularly, the content of alkali metal ions is 20 ppb or less, preferably 10 ppb or less, based on TAAC.

The production of the above TAAH aqueous solution is carried out by subjecting the above high-purity TAAC aqueous solution to electrolysis and electrodialysis, that is, a so-called electrolysis-dialysis. The chlorine ions of TAAC are exchanged with hydroxyl ions by the electrolysis-dialysis to form TAAH.

As a method for the above electrolysis-dialysis, conventionally known methods are employed without particular restriction. Generally speaking, a TAAC aqueous solution is supplied to an electrolytic/electrodialytic cell having an intermediate chamber(s) formed by arranging only a cation exchange membrane or a combination of a cation exchange membrane and an anion exchange membrane between a cathode and an anode, an acid is supplied to an anode chamber formed on one side of the cell, and the TAAH aqueous solution is obtained from the cathode chamber formed on the other side of the cell.

Electrolysis-dialysis is carried out by supplying an aqueous solution of an acid such as hydrochloric acid to the anode chamber, the TAAC aqueous solution to the intermediate chambers formed by cation exchange membranes and an anion exchange membrane and high-purity water, particularly ultrapure water or a high-purity TAAH aqueous solution to the cathode chamber.

By carrying out the above electrolysis-dialysis method, a TAAH aqueous solution containing an extremely small amount of metal ions can be obtained from the cathode chamber. But, in this case, chlorine ions contained in the TAAC aqueous solution may move to the cathode chamber by diffusion, so that the obtained TAAH aqueous solution is contaminated with chlorine ions.

To obtain a TAAH aqueous solution of higher-purity by preventing the diffusion of chlorine ions effectively, an electrolysis-dialysis cell is preferably used which is, for example, constituted by arranging two or more cation exchange membranes 3-a and 3-b, anion exchange membrane 4 and cation exchange membrane 5 from the cathode side between the cathode 1 and the anode 2 sequentially to form chambers defined by these ion exchange membranes, as shown in FIG. 1. And, electrolysis is carried out by supplying water or a high-purity TAAH aqueous solution to the cathode chamber 101 comprising a cathode, an aqueous solution containing an electrolyte essentially composed of TAAH to the intermediate chamber 102 formed by two cation exchange membranes, the high-purity TAAC aqueous solution obtained by the above method to the intermediate chamber 103 formed by the cation exchange membrane 3-b on the cathode side and the anion exchange membrane 4, and an aqueous solution of an acid to the intermediate chamber 104 formed by the anion exchange membrane 4 and the cation exchange membrane 5 that is present on the anode side and the anode chamber 105 comprising the anode 2, and applying a direct current between the electrodes.

In the above method, an aqueous solution of hydrochloric acid is advantageously used as the aqueous solution of an acid to be supplied to the intermediate chamber 104, and an aqueous solution of sulfuric acid is advantageously used as the aqueous solution of an acid to be supplied to the anode chamber 105. The concentration of chlorine ions contained in the electrolyte aqueous solution to be supplied to the intermediate chamber 102 is preferably adjusted to 30 ppb or less, more preferably 20 ppb or less to reduce the concentration of chlorine ions contained in the obtained TAAH aqueous solution to a target value.

According to the above method, it is possible to reduce the concentration of chlorine ions contained in the obtained TAAH aqueous solution to 5 ppb or less.

Known cation exchange membranes and anion exchange membranes which have been conventionally used in the production of a TAAH aqueous solution by electrolysis-dialysis can be used without particular restriction as the cation exchange membrane and anion exchange membrane used for the above electrolysis-dialysis. For example, the cation exchange membrane is a membrane having a sulfonic acid group, carboxylic acid group, phosphoric acid group or the like; and the anion exchange membrane is a membrane having at least one of strong basic ion exchange groups such as a quaternary ammonium salt group, sulfonium salt group, phosphonium salt group or the like and primary, secondary and tertiary amines bonded. The substrate of the ion exchange membrane is selected from hydrocarbon-, fluorocarbon- and perfluorocarbon-based resins. Particularly, the cation exchange membrane that constitutes the cathode chamber is preferably made from a perfluorocarbon resin which is stable in a basic atmosphere and has excellent durability, and a perfluorocarbon-based ion exchange membrane having oxidation resistance is preferably used for the ion exchange membrane in contact with the anode chamber because an oxidative gas(es) such as halogen gas, oxygen gas or the like generate(s) in the anode chamber.

A so-called insoluble electrode of carbon, platinum-coated titanium, ruthenium, iridium-coated titanium or the like is advantageously used as the anode. A material which is stable in a strong basic atmosphere and has a low overpotential, such as SUS316, platinum, Raney nickel or the like, is advantageously used as the cathode.

In the above electrolysis-dialysis, the current density is suitably 1 to 50 amp/dm$^2$ and the temperature is preferably controlled to a temperature not higher than 90° C., more preferably 30 to 50° C.

The high-purity TAAH aqueous solution which is the object of the present invention cannot be obtained unless the high-purity TAAC obtained by the above method is subjected to the above electrolysis-dialysis. In other words, even when electrolysis-dialysis is carried out under the above conditions, if TAAC is contaminated by impurities, the impurities, particularly univalent ions such as sodium ions and potassium ions, are directly introduced to the cathode chamber in which TAAH is obtained, without being inhibited by the above ion exchange membranes.

Further, ions having a valence of 2 or higher inhibited in the electrolytic cell may cause, in some case, fouling in the ion exchange membranes during long-term operation, thereby hampering stable operation or inviting re-inclusion into a product by diffusion.

In the present invention, it is preferred that the raw materials and purified product present in a section extending from the distillation columns 203 and 204 up to the electrolysis-dialysis cell via the reactor 205 shown in FIG. 1 should not come substantially in contact with the open air in order to obtain a higher-purity TAAH aqueous solution. Stated more specifically, such methods can be employed that the gas-phase portion of the reactor is sealed with an inert gas such as nitrogen gas or the like; the electrolysis-dialysis cell is constructed in a tight-closed type like a filter press type cell; the lines connecting the devices are made air-tight; and the like.

As is understood from the above description, according to the method of the present invention, an extremely high-purity TAAH aqueous solution can be obtained efficiently, and the method of the present invention is extremely useful for the industrial production of a high-purity TAAH aqueous solution.

The amount of metal ion impurities contained in the TAAH aqueous solution is 500 ppb or less, preferably 100 ppb or less, based on the TAAH. Particularly, the amount of alkali metal ions is 20 ppb or less, preferably 10 ppb or less, based on the TAAH. In the TAAH aqueous solution obtained from the preferred electrolysis-dialysis device shown in FIG. 1, it is possible to reduce the concentration of chlorine ions to 5 ppb or less.

The following examples are provided for the purpose of further illustrating the present invention but are in no way to be taken as limiting. The metal ion impurities were measured by inductively coupled plasma mass spectrometry (IPC-MS).

EXAMPLE 1

Liquefied trimethylamine containing more than 1,000 ppb of metal ions was supplied to a distillation column 203 having a demister 201 at the column top and gasified to form trimethylamine having a reduced metal ion concentration of 50 ppb. Then, the obtained trimethylamine was supplied to a reactor 205 equipped with an external jacket. The above distillation column, reactor and pipes connecting these were lined with PTFE. Meanwhile, liquefied methyl chloride containing more than 1,000 ppb of metal ions was also supplied to a distillation column 204 having a demister 202 at the column top and gasified to form methyl chloride having a reduced metal ion concentration of 50 ppb. The obtained methyl chloride was supplied to the above reactor 205. The molar ratio of the supplied raw materials is 1.1 mols of methyl chloride per 1 mol of trimethylamine.

In the above operation, ultrapure water was in advance contained in the reactor and the temperature of the reactor was controlled so as to maintain the reaction temperature at 40° C. The amount of supplied gas was adjusted such that the pressure inside the reactor is to be about 3 kg/cm$^2$.

The above reaction was carried out until the concentration of a tetramethyl ammonium chloride aqueous solution produced in the reactor became 50 wt %, and then, the pressure inside the reactor was reduced to 500 Torr by an ejector, and methyl chloride as a raw material was mainly removed. Waste gas going into the ejector was brought into contact with ultrapure water to absorb raw materials contained therein, and supplied to the reaction system upon being counted as part of the amount of methyl chloride to be supplied.

The content of impurities contained in the obtained tetramethyl ammonium chloride aqueous solution, based on the solute (tetramethyl ammonium chloride) and the aqueous solution is shown in Table 1.

TABLE 1

| Analyzed item | Unit | Analytical results Based on solute | Analytical results Based on solution |
|---|---|---|---|
| silver | ppb | <0.2 | <0.1 |
| aluminum | ppb | <0.4 | <0.2 |
| gold | ppb | <2 | <1 |
| barium | ppb | <0.6 | <0.3 |
| calcium | ppb | <2 | <1 |
| cadmium | ppb | <0.4 | <0.2 |
| cobalt | ppb | <0.4 | <0.2 |
| chromium | ppb | <1.2 | <0.6 |
| copper | ppb | <1.0 | <0.5 |
| iron | ppb | <1.0 | <0.5 |
| potassium | ppb | <1.0 | <0.5 |
| lithium | ppb | <0.1 | <0.05 |
| magnesium | ppb | <0.2 | <0.1 |
| manganese | ppb | <0.2 | <0.1 |
| sodium | ppb | <2 | <1 |
| nickel | ppb | <2 | <1 |
| lead | ppb | <0.4 | <0.2 |
| strontium | ppb | <0.6 | <0.3 |
| zinc | ppb | <2 | <1 |

The tetramethyl ammonium chloride aqueous solution obtained by the above method was subjected to an electrolysis-dialysis using devices shown in FIG. 1, in which intermediate chambers are formed by arranging cation exchange membranes and an anion exchange membrane between a cathode and an anode.

SUS316 was used as the cathode and a titanium plate plated with platinum was used as the anode. Naphion 901 (a product of E. I. Du Pont) was used as the cation exchange membrane and AM-1 (a product of Tokuyama Corporation) was used as the anion exchange membrane.

The electrolysis-dialysis were carried out by supplying a 0.5 N hydrochloric acid aqueous solution to the anode chamber 105 and the intermediate chamber 104, the tetramethyl ammonium hydroxide aqueous solution obtained in Example 1 to the intermediate chamber 103 formed by a cation exchange membrane and an anion exchange membrane, a 2.5 N TAAH aqueous solution having a chlorine ion concentration of 20 ppb or less to the intermediate chamber 102, and ultrapure water to the cathode chamber.

A pipe connecting the electrolysis-dialysis cell and the reactor, and pipes and a tank provided for the electrolysis-dialysis cell were lined with PTFE. A filter press type cell was used as the electrolysis-dialysis cell and the frame of each chamber was made from PP. A gas phase portion of the reactor was supplied with a nitrogen gas and sealed.

The current density was adjusted to 15 amp/dm$^2$ and the temperature was maintained at 40° C.

A 2.5 N tetramethyl ammonium hydroxide aqueous solution was continuously obtained from the cathode chamber 101. The properties of the obtained tetramethyl ammonium hydroxide aqueous solution and the content of impurities contained therein are shown in Table 2.

TABLE 2

| Analyzed item | Unit | Analytical results Based on solute | Based on solution |
|---|---|---|---|
| TMAH concentration | Normal | 2.5 | |
| silver | Normal | <0.4 | <0.1 |
| aluminum | Normal | <0.9 | <0.2 |
| gold | Normal | <4.4 | <1 |
| barium | Normal | <1.3 | <0.3 |
| calcium | Normal | <4.4 | <1 |
| cadmium | Normal | <0.9 | <0.2 |
| cobalt | Normal | <0.9 | <0.2 |
| chromium | Normal | <2.6 | <0.6 |
| copper | Normal | <2.2 | <0.5 |
| iron | Normal | <2.2 | <0.5 |
| potassium | Normal | <2.2 | <0.5 |
| lithium | Normal | <0.22 | <0.05 |
| magnesium | Normal | <0.4 | <0.1 |
| manganese | Normal | <0.4 | <0.1 |
| sodium | Normal | <4.4 | <1 |
| nickel | Normal | <4.4 | <1 |
| lead | Normal | <0.9 | <0.2 |
| strontium | Normal | <1.3 | <0.3 |
| zinc | Normal | <4.4 | <1 |
| chlorine | Normal | <13.1 | <3 |

COMPARATIVE EXAMPLE 1

The reactor, the pipe connecting the electrolysis-dialysis cell and the reactor and the pipes and tank provided for the electrolysis-dialysis cell were made from stainless steel and not lined with PTFE. A reaction was carried out without supplying nitrogen gas to the gas-phase portion of the reactor.

Trimethylamine and methyl chloride each containing more than 1,000 ppb of metal ions were first supplied from the respective bombs to isopropanol in the same ratio as in Example 1 and reacted with each other to obtain a tetramethyl ammonium chloride solution. Thereafter, the solution was filtrated and dried to obtain solid tetramethyl ammonium chloride. The obtained solid tetramethyl ammonium chloride was then dissolved in ultrapure water to prepare an aqueous solution having the same concentration as in Example 1.

The content of impurities contained in the thus obtained tetramethyl ammonium chloride aqueous solution is shown in Table 3.

TABLE 3

| Analyzed item | Unit | Analytical results Based on solute | Based on solution |
|---|---|---|---|
| silver | ppb | <0.2 | <0.1 |
| aluminum | ppb | 2.0 | 1.0 |
| gold | ppb | <2 | <1 |
| barium | ppb | 6.0 | 3.0 |
| calcium | ppb | 100 | 50 |
| cadmium | ppb | <0.4 | <0.2 |
| cobalt | ppb | <0.4 | <0.2 |
| chromium | ppb | 29.2 | 14.6 |
| copper | ppb | 13.6 | 6.8 |
| iron | ppb | 99.0 | 49.5 |
| potassium | ppb | 46.6 | 23.3 |

TABLE 3-continued

| Analyzed item | Unit | Analytical results Based on solute | Based on solution |
|---|---|---|---|
| lithium | ppb | 0.64 | 0.32 |
| magnesium | ppb | 3.6 | 1.8 |
| manganese | ppb | 2.0 | 1.0 |
| sodium | ppb | 230 | 115 |
| nickel | ppb | 2 | 1 |
| lead | ppb | 4.8 | 2.4 |
| strontium | ppb | 6.2 | 3.1 |
| zinc | ppb | 8 | 4 |

The tetramethyl ammonium chloride aqueous solution obtained by the above method was subjected to an electrolysis-dialysis using membranes in the same manner as in Example 1.

The properties of the obtained tetramethyl ammonium hydroxide aqueous solution and the content of impurities contained therein are shown in Table 4.

TABLE 4

| Analyzed item | Unit | Analytical results Based on solute | Based on Solution |
|---|---|---|---|
| TMAH concentration | Normal | 2.5 | |
| silver | ppb | <0.4 | <0.1 |
| aluminum | ppb | 3.9 | 0.9 |
| gold | ppb | <4.4 | <1 |
| barium | ppb | 6.6 | 1.5 |
| calcium | ppb | 382 | 87 |
| cadmium | ppb | <0.9 | <0.2 |
| cobalt | ppb | <0.9 | <0.2 |
| chromium | ppb | 39.1 | 8.9 |
| copper | ppb | 15.4 | 3.5 |
| iron | ppb | 108 | 24.7 |
| potassium | ppb | 112 | 25.6 |
| lithium | ppb | 0.79 | 0.18 |
| magnesium | ppb | 4.8 | 1.1 |
| manganese | ppb | 3.9 | 0.9 |
| sodium | ppb | 632 | 144 |
| nickel | ppb | <4.4 | <1 |
| lead | ppb | 4.8 | 1.1 |
| strontium | ppb | 7.9 | 1.8 |
| zinc | ppb | 13 | 3 |
| chlorine | ppb | <13 | <3 |

Although the accumulation of ions having a valence of 2 or higher in the cell was seen, it was observed that most of metal impurities contained in the raw material (tetramethyl ammonium chloride) passed through the cation exchange membranes and were carried to the tetramethyl ammonium hydroxide aqueous solution.

We claim:

1. A method of producing a high-purity tetraalkylammonium hydroxide aqueous solution comprising the steps of:

reacting trialkylamine and alkyl chloride, both having a metal ion impurity content of 500 ppb or less, with each other in ultrapure water to form an aqueous solution of tetraalkylammonium chloride, and then, subjecting the resulting aqueous solution of tetraalkylammonium chloride to electrolysis and electrodialysis to produce a high-purity tetraalkylammonium hydroxide aqueous solution.

2. The method of claim 1, wherein the trialkylamine and the alkyl chloride both containing, as metal ion impurities, sodium ions and potassium ions each in an amount of 50 ppb or less are used.

3. The method of claim 1, wherein processes from the reaction for forming the aqueous solution of tetraalkylammonium chloride up to the electrolysis and electrodialysis for producing the high-purity tetraalkylammonium hydroxide aqueous solution are carried out without permitting them to contact with the open air.

4. The method of claim 1, wherein the high-purity tetraalkylammonium hydroxide aqueous solution contains metal ion impurities in an amount of 500 ppb or less in terms of the weight basis of tetraalkylammonium hydroxide.

5. The method of claim 1, wherein alkyl chloride is used in a stoichiometrically excessive amount with respect to trialkylamine in the reaction between trialkylamine and alkyl chloride.

6. The method of claim 1, wherein unreacted raw materials are removed by evaporation from the aqueous solution of tetraalkylammonium chloride and absorbed in ultrapure water, and the ultrapure water containing the unreacted raw materials is recycled to a reaction system as part of reaction raw materials.

7. The method of claim 1, wherein before the aqueous solution of tetraalkylammonium chloride is subjected to electrolysis and electrodialysis, it is concentrated to be adjusted to a desired concentration by removing water from the aqueous solution of tetraalkylammonium chloride by evaporation.

8. The method of claim 1, wherein trialkylamine and alkyl chloride both of which have been purified so as to contain metal ion impurities to 100 ppb or less are used.

9. The method of claim 1, wherein the reaction for obtaining an aqueous solution of tetraalkylammonium chloride and the electrolysis and electrodialysis of the aqueous solution of tetraalkylammonium chloride are carried out using devices of which at least the inside surfaces are made from a material that does not substantially elute metal ions and which are connected with air-tight pipes, of which at least the inside surfaces are made from a material that does not substantially elute metal ions.

* * * * *